United States Patent [19]

Jäger

[11] 4,111,817
[45] Sep. 5, 1978

[54] HETEROCYCLIC NITROGEN COMPOUNDS, PROCESS FOR THEIR MANUFACTURE AND THEIR USE

[75] Inventor: Horst Jäger, Bettingen, Switzerland

[73] Assignee: Ciba-Geigy Corporation, Ardsley, N.Y.

[21] Appl. No.: 762,552

[22] Filed: Jan. 25, 1977

Related U.S. Application Data

[62] Division of Ser. No. 639,311, Dec. 10, 1975, abandoned.

[30] Foreign Application Priority Data

Dec. 20, 1974 [CH] Switzerland ............... 17037/74

[51] Int. Cl.$^2$ ........................................ D06M 13/46
[52] U.S. Cl. ........................ 252/8.8; 8/115.6; 428/96
[58] Field of Search .............. 252/8.8 AH, 8.8 R; 8/115.6; 428/96

[56] References Cited

U.S. PATENT DOCUMENTS

| | | | |
|---|---|---|---|
| 3,063,870 | 11/1962 | Wakeman et al. | 252/8.8 R |
| 3,379,685 | 4/1968 | Preininger et al. | 260/47 |
| 3,804,852 | 4/1974 | Haemmerle et al. | 260/326 |
| 3,910,759 | 10/1975 | Sthare et al. | 8/115.6 |

OTHER PUBLICATIONS

Sekiya et al., "Chem. Abstracts," vol. 73, p. 45020e, 1970.
Brown et al., "Chem. Abstracts," vol. 64, p. 6606 (1966).
Eitingon et al., "Chem. Abst.," vol. 61, p. 14871f (1964).

Primary Examiner—William E. Schulz
Attorney, Agent, or Firm—Edward McC. Roberts; Prabodh I. Almaula

[57] ABSTRACT

Heterocyclic nitrogen compounds of the formula

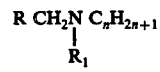

are provided, wherein R is a succinimide, maleinimide, or phthalimide radical or a lactam radical containing 5 to 11 —(CH$_2$)— groups in the heterocyclic ring, R$_1$ is hydrogen or C$_n$H$_{2n+1}$ and $n$ is an integer from 1 to 24.

These compounds are useful for finishing synthetic organic fibrous material, in particular for providing it with an antistatic finish and optionally improving the dirt repellency, optionally in admixture with polymers; said compounds or mixtures are applied to the fibrous material from aqueous or organic solutions or from emulsions, and subsequently dried at elevated temperature.

9 Claims, No Drawings

HETEROCYCLIC NITROGEN COMPOUNDS, PROCESS FOR THEIR MANUFACTURE AND THEIR USE

This is a divisional of application Ser. No. 639,311, filed on Dec. 10, 1975, now abandoned.

It is known to provide synthetic organic fibrous material with an antistatic or also dirt repellent finish. It is also known that a marked deterioration of the antisoiling behaviour occurs in many antistatic finishes. A further frequently observed disadvantage of the finished fibrous material is the poor resistance to yellowing on exposure to light and/or heat.

It is the object of the present invention to provide heterocyclic compounds with antistatic properties which, in admixture with certain polymeric compounds, largely overcome the disadvantages referred to above.

The present invention therefore provides heterocyclic nitrogen compounds of formula

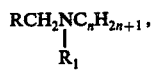  (1)

wherein R is

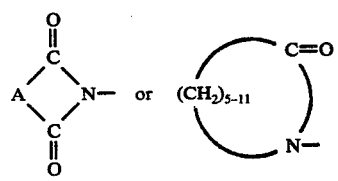

A is —$CH_2CH_2$—, —$CH=CH$— or

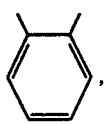, $R_1$ is hydrogen or $C_nH_{2n+1}$ and $n$ is an integer from 1 to 24.

The invention also provides a process for the manufacture of the compounds of formula (1) as well as a method of using these compounds for finishing synthetic organic fibrous material, in particular for providing it with an antistatic finish and optionally simultaneously improving the dirt repellency, optionally in admixture with polymers, said compounds or mixtures being applied to the fibrous material from aqueous or organic solutions or from emulsions, and subsequently dried at elevated temperature.

In addition, the invention also provides the preparations for carrying out the method of application.

The compounds of the present invention of formula (1) are N-substituted succinimides, maleinimides, phthalimides and lactams containing 5 to 11 —($CH_2$)— groups in the heterocyclic ring and wherein the radical R is in particular

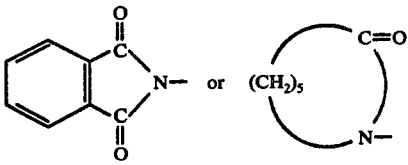

The substituent $R_1$ is hydrogen or the radical $C_nH_{2+1}$, wherein $n$ is an integer from 1 to 24. The radical $C_nH_{2n+1}$ can be straight-chain or branched alkyl of 1 to 24 carbon atoms, for example methyl, ethyl, propyl, isopropyl, butyl or isobutyl, hexyl, octyl, decyl, dodecyl, myristyl, palmityl, stearyl, arachidyl or behenyl. Preferably $n$ is an integer from 12 to 18.

Preferred compounds of formula (1) have the formula

  (2)

wherein R is as defined hereinbefore, $R_2$ is hydrogen, methyl or the radical $C_{n_1}H_{2n_1+1}$ and $n_1$ is an integer from 6 to 24, preferably from 12 to 18.

Particularly suitable compounds are also those of formula

  (3)

wherein R is as defined hereinbefore and $n_2$ is an integer from 6 to 18 or 12 to 18.

Examples of compounds of formulae (2) and (3) are:

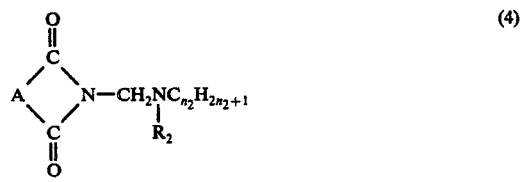  (4)

and especially

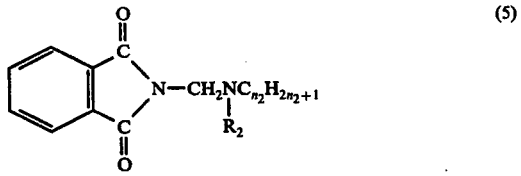  (5)

or

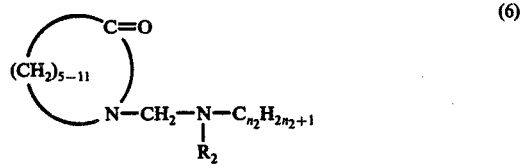  (6)

and especially

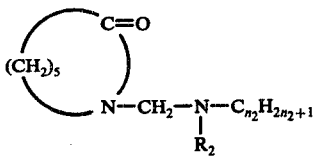
(7)

wherein A, $R_2$ and $n_2$ are as defined hereinbefore.

The compounds of formula (1) are obtained by reacting succinimides, maleinimides or lactams containing 5 to 11 —$CH_2$— groups in the heterocyclic ring, in particular phthalimide or caprolactam, with formaldehyde and mono- or dialkylamines which contain 1 to 24 carbon atoms in the alkyl moiety, at elevated temperature.

The compounds of formula (2) are obtained by reacting the cited imides, or lactams with formaldehyde and with monoalkylamines containing 6 to 24 carbon atoms or with methylalkylamines which contain 6 to 24 carbon atoms in the alkyl moiety, in corresponding manner.

The particularly preferred compounds of formula (3) are obtained by reacting the cited imides or lactams with monoalkylamines containing 6 to 18 or 12 to 18 carbon atoms. Examples of monoalkylamines are laurylamine (of 12 carbon atoms) and cetylamine (of 16 carbon atoms), and examples of dialkylamines are dilaurylamine, distearylamine (of 18 carbon atoms) and di-2-ethylhexylamine (of 8 carbon atoms).

The imides and lactams used as starting materials are known chemical compounds.

The manufacture of the compounds of the present invention of formula (1) can be carried out without solvents or in organic solvents, where appropriate also in organic-aqueous systems, by reacting the starting materials at 80° to 120° C. The reaction time can be from about 3 to 24 hours. Examples of suitable solvents are: halogenated hydrocarbons, such as tetrachloromethane, perchloroethylene, trichloroethylene, ethers, such as dioxan, or conventional aromatic solvents, for example benzene, toluene or xylene. The solvents can contain up to 20% of water, referred to their volume.

The compounds of formula (1) are suitable antistatic agents for finishing synthetic organic fibrous materials. Because of their surface-active properties, they can also be used as non-corrosive antistatic lubricants or as detergents, for example for removing non-fixed dye from substrates that are dyed from solvents.

In combination with at least one homopolymer derived from monomers of the formulae

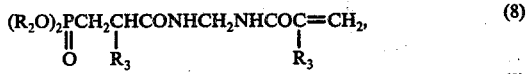
(8)

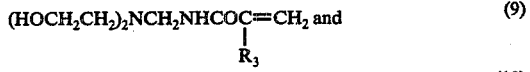
(9)

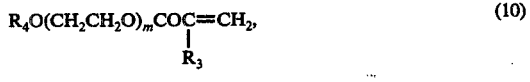
(10)

wherein $R_2$ is straight-chain or branched alkyl of 1 to 8 carbon atoms, $R_3$ is hydrogen or methyl, $R_4$ is alkyl of 1 to 6 carbon atoms and $m$ is an integer from 6 to 15, preferably from 6 to 10, and, optionally, with further homopolymers or copolymers, improved antistatic effects are obtained without a simultaneous deterioration in the dirt repellency of the finished textile material.

The further homopolymers or copolymers are not derived from the monomers of formulae (8) to (10).

$R_2$ and $R_4$ are in particular alkyl of 1 to 4 carbon atoms, preferably methyl and ethyl.

The homopolymers and copolymers can have molecular weights of about 2000 to 50,000.

The monomers of formulae (8) to (10) are known compounds. The compounds of formula (4) are known, for example, from Swiss Pat. No. 445 126; those of formula (9) from German Auslegeschrift No. 1,111,825; and those of formula (10) from U.S. Pat. No. 2,839,430.

Preferred mixtures are those consisting of compounds of formula (1) with homopolymers derived from the monomers of formulae (8), (9) and (10). The mixtures usually contain up to a maximum of 30 percent by weight, in particular 5 to 20 percent by weight of the compounds of formula (1) and accordingly at least 70 percent by weight, preferably 80 to 95 percent by weight of the homopolymers and copolymers.

Optionally, it is also possible to use a further ethylenically unsaturated comonomer for the manufacture of the copolymers.

The compounds of formulae (8) to (10) have, for example, the formulae

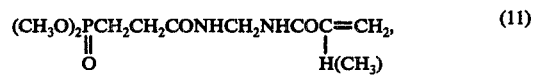
(11)

(12)

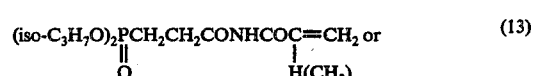
(13)

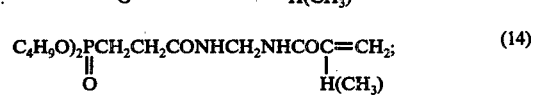
(14)

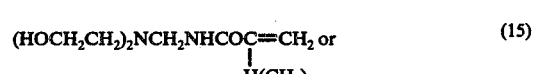
(15)

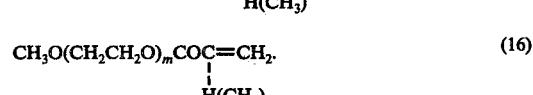
(16)

Examples of suitable monomers for the manufacture of further homopolymers or copolymers that can be used if appropriate are:

(a) vinyl esters of organic acids, for example vinyl acetate, vinyl formiate, vinyl butyrate, vinyl benzoate, (b) vinyl alkyl ketones, such as vinyl methyl ketone, (c) vinyl halides, such as vinyl chloride, vinyl fluoride, vinylidene chloride.

(d) derivatives of the acrylic acid series, such as acrylic nitrile or acrylic amide and preferably derivatives thereof which are substituted at the amide nitrogen, for example N-methylolacrylic amide, N-methylolacrylic amide alkyl ethers, for example methylolacrylic amide monomethyl ether, N,N-dihydroxy-ethylacrylic amide, N-tert. butylacrylic amide and hexamethylolmelamine triacrylic amide, and (e) α,β-unsaturated mono- or dicarboxylic acids containing 3 to 5 carbon atoms and esters thereof, for example acrylic acid, methacrylic acid, α-chloroacrylic acid, crotonic acid, maleic acid, fumaric acid, or itaconic acid and esters thereof with mono- or dialcohols containing 1 to 18 carbon atoms, epoxides or phenols, for example ethyl acrylate, methylmethacrylate, glycidyl acrylate, butylacrylate, isobutylacrylate, acrylic acid monoglycol ester, dodecylacrylate or 2-ethylhexylacrylate.

Polymerisable olefins, such as isobutylene, butadiene or 2-chlorobutadiene, can also be used.

It is preferred to use acrylic acid, methacrylic acid, the esters thereof with 1 to 8 carbon atoms in the ester moiety, for example methyl-methacrylate, isobutylacrylate, 2-ethylhexylacrylate, as well as acrylic amide and methacrylic amide, which can be N-methylolated and optionally etherified, for example N-methylolacrylic amide, N-methylolacrylic amide methyl ether.

The manufacture of the polymers by homo- or copolymerisation is effected by conventional methods, for example preferably by polymerisation in aqueous emulsion or also by solvent polymerisation in a solvent suitable for this purpose, for example acetone, benzene, sym. dichloroethane, ethyl acetate or trifluoromethylbenzene.

The polymerisation is effected advantageously with the application of heat, preferably to the boiling temperature of the solvent, and accompanied by the addition of peroxide or other catalysts which form free radicals and which are soluble in the reaction medium, for example benzoyl peroxide, lauroyl peroxide, $\alpha,\alpha'$-azobisisobutyrodinitrile or potassium sulphate or in the presence of redox systems, for example potassium peroxide disulphate/sodium bisulphite or ferrosulphate. In the manufacture of copolymers, the monomers can be used in the polymerisation reaction in any desired quantity ratios. In the manufacture of copolymers from, for example monomer components, the molar ratio can be for example 1:10 to 10:1, preferably 1:5 to 5:1.

Depending on the nature of the polymerisation conditions and of the monomeric starting materials used, the polymer compounds are obtained in the form of viscous solutions or of emulsions.

The polymerisation is preferably carried out within a reaction time that is so chosen that a virtually quantitative conversion of the monomer into the polymer is attained. The maximum reaction time depends on the catalyst used and the polymerisation temperature and also on other conditions, but it is generally in the range of 0.5 to 24 hours.

The polymerisation temperature depends in turn on the chosen catalyst. In the case of emulsion polymerisation in aqueous medium it is usually in the range of 20° to 90° C, preferably 40° to 80° C. Wherever possible, the polymerisation is carried out at atmospheric pressure.

In emulsion polymerisation the monomer or monomers to be polymerised are polymerised jointly in an aqueous solution of an emulsifier, optionally under nitrogen.

The concentration of the polymerisation catalyst is usually between 0.1 and 2%, referred to the weight of the monomers.

Suitable emulsifiers are cationic, anionic or non-ionic surface-active agents. The hydrophobic constituent of the emulsifier can be a hydrocarbon or a fluorinated hydrocarbon.

Suitable cationic emulsifiers are, for example, quaternary ammonium salts or amine salts which contain at least one long-chain alkyl or fluoro-alkyl group, or a benzene or naphthalene group which is highly substituted by alkyl to yield the hydrophobic constituent.

Further suitable emulsifiers are the non-ionic surfactants in which the hydrophilic constituent is a poly(ethoxy) group and the hydrophobic constituent is either a hydrocarbon or a fluorinated hydrocarbon group, e.g. the ethylene oxide condensates of alkylphenols, alkanols, alkylamines, alkylthiols, alkylcarboxylic acids, fluoroalkylcarboxylic acids, fluoroalkylamides and the like. Anionic emulsifiers are, for example the sulphuric acid or phosphoric acid esters of the cited ethylene oxide condensates of long-chain alkylphenols, fatty alcohols, and fatty amines.

In the solvent polymerisation, the monomer or monomers are dissolved in a suitable solvent, such as fluorinated solvents, for example hexafluoroxylene, benzotrifluoride, or mixtures thereof with acetone and/or ethyl acetate, and polymerised in a reaction vessel with the addition of initiators, such as azobisisobutyronitrile or other azo initiators, in concentrations of 0.1 to 2%, at 40° to 100° C optionally under nitrogen.

Preferred solvents are hexafluoroxylene, benzotrifluoride or fluorinated hydrocarbons.

The preparations or compositions for the application of the compounds of the present application to fibrous material contain as a rule 1 to 30 percent by weight of at least one compound of formula (1) and optionally 1 to 30 percent by weight of homopolymers derived from the monomers of formulae (8) to (10) and further homopolymers or copolymers. The indicated percentages by weight refer to the total weight of the preparations or compositions.

The preparations for providing synthetic organic fibrous material with an antistatic and dirt repellent finish contain, for example 1 to 30, in particular 1 to 20 and preferably 1 to 10, percent by weight of at least one compound of formula (1) and 1 to 30, preferably 1 to 20, percent by weight of at least one homopolymer derived from monomers of formulae (8) to (10), and, if appropriate, 1 to 10, preferably 1 to 5, percent by weight of further homopolymers, the total content of the components in the preparations being at most 60 percent by weight.

Suitable types of synthetic organic textile material that can be treated with the monomeric or polymeric compounds are those, for example, obtained from polyamides, polyesters, polyacrylonitrile or polyolefins. It is also possible to finish with advantage blends of these materials, optionally together with other fibres, for example cotton or wool. The textiles can be in the form of threads, fibres, flocks, non-wovens, woven or knitted fabrics or of piece goods, for example floor coverings, or other domestic textiles, such as upholstery fabrics, furnishing materials, curtains or wall coverings. The textile materials can be undyed or dyed by known methods.

The preparations or compositions which contain the monomeric or polymeric compounds can be applied to the substrate in conventional known manner at room temperature or also at elevated temperature, for example at 20° to 40° C. They can also contain further additives customarily used in textile finishing.

The pH of the preparations can be approximately 2 to 10, preferably 5 to 8. The total solids content of the preparations will be at most 60 percent by weight, in particular 1 to 40 and preferably 1 to 30 percent by weight.

The substrates can be treated with solutions or emulsions of the monomeric or polymeric compounds. The monomers can be applied, for example, from a solution in an organic solvent to the textile material and, after evaporation of the solvent, fixed on the fabric by heat. Polymers can also be applied to the fabrics from suitable solvents. The fixation on the substrates can be effected, if desired, in the presence of a conventional curing catalyst, for example magnesium chloride or ammonium chloride.

Fabrics can be impregnated, for example, by the exhaustion process or on a padder that is charged with the preparation at room temperature. The impregnated material is subsequently dried at 80° to 200° C, preferably at 120° to 160° C.

Further methods of application are, for example, spraying, brushing, roller coating or slop-padding. The compounds of the present invention are applied to the substrate in amounts of 0.1 to 10, preferably of 0.5 to 5, percent by weight.

The textile material finished according to the invention is antistatic, i.e. it releases no troublesome electrical discharges on being touched or walked on. The antisoiling effect and also the fastness to rubbing and light and the soft handle are not impaired by the finish.

The finish also has good permanency, i.e. it is resistant to washes with conventional household detergents or to cleaning with customary organic solvents. Carpeting materials, for example, can be repeatedly brushed, vacuum cleaned or shampooed without any loss of the finishing effects.

The following Examples illustrate the present invention in more detail without implying any restriction to what is described therein. The parts and percentages are by weight unless otherwise indicated.

EXAMPLE 1

73.5 g (0.5 mole) of phthalimide are reacted with 15 g (0.5 mole) of formaldehyde and 92.5 g (0.5 mole) of laurylamine in benzene for 10 hours at 80° C. The solvent is subsequently distilled off in a water-jet vacuum.

Yield: 168 g (=97.7%) of the compound of formula

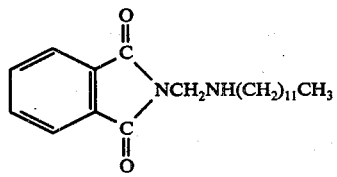

(101)

Analysis: calculated: N 8.14; found: N 8.0.
Mass spectrum: M = 344 (theoretical value: 344).

EXAMPLE 2

73.5 g (0.5 mole) of phthalimide are reacted with 15 g (0.5 mole) of formaldehyde and 120.5 g (0.5 mole) of cetylamine as in Example 1.

Yield: 198 g (=99%) of the compound of formula

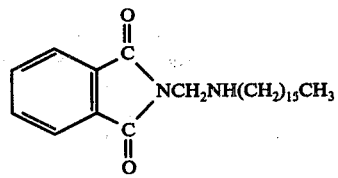

(102)

Analysis: calculated: N 7.0; found: N 7.3.
Mass spectrum: M = 400 (theoretical value: 400).

EXAMPLE 3

73.5 g (0.5 mole) of phthalimide are reacted with 15 g (0.5 mole) of formaldehyde and 285.5 g of distearylamine (0.5 mole) as in Example 1. Toluene is used as solvent.

Yield: 332 g (=97.1%) of the compound of formula

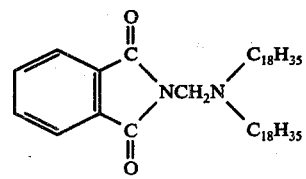

(103)

Analysis: calculated: N 4.4; found: N 4.2.

EXAMPLE 4

56.5 g (0.5 mole) of caprolactam are reacted with 15 g (0.5 mole) of formaldehyde and 92.7 g (0.5 mole) of laurylamine as in Example 1.

Yield: 146.6 g (=94.7%) of the compound of formula

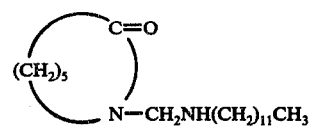

(104)

Analysis: calculated: N 9.02; found: N 8.75.
Mass spectrum: M = 310 (theoretical value: 310).

EXAMPLE 5

56.6 g (0.5 mole) of caprolactam are reacted with 15 g (0.5 mole) of formaldehyde and 120.5 g (0.5 mole) of cetylamine as in Example 1. Toluene is used as solvent Yield: 178 g (=97%) of the compound of formula

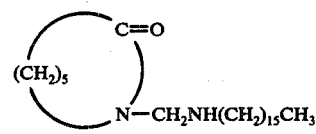

(105)

Analysis: calculated: N 7.64; found: N 7.1.
Mass spectrum: M 32 366 (theoretical value: 366).

EXAMPLE 6

56.5 g (0.5 mole) of caprolactam are reacted with 15 g (0.5 mole) of formaldehyde and 176.5 g (0.5 mole) of dilaurylamine as in Example 1. Toluene is used as solvent.

Yield: 210 g (=92.5%) of the compound of formula

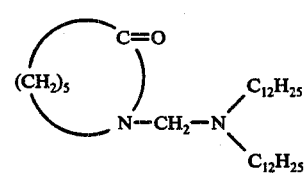

(106)

Analysis: calculated: N 5.85; found: N 6.0.

EXAMPLE 7

49.5 g (0.5 mole) of succinimide are reacted with 15 g (0.5 mole) of formaldehyde and 92.5 g (0.5 mole) of laurylamine as in Example 1. Toluene is used as solvent.
Yield: 115 g (=83.94%) of the compound of formula $$\begin{array}{c} CH_2-C \\ | \quad\quad\quad\,\, \diagdown \\ \quad\quad\quad\quad\quad\, N-CH_2-NH-C_{12}H_{25} \\ | \quad\quad\quad\,\, \diagup \\ CH_2-C \end{array}$$ (107)

Analysis: calculated: N 9.45; found: N 9.2.

EXAMPLE 8

49.5 g (0.5 mole) of succinimide are reacted with 15 g (0.5 mole) of formaldehyde and 120.5 g (0.5 mole) of cetylamine as in Example 1. Toluene is used as solvent.
Yield: 176 g (=100%) of the compound of formula $$\begin{array}{c} CH_2-C \\ | \quad\quad\quad\,\, \diagdown \\ \quad\quad\quad\quad\quad\, N-CH_2-NH-C_{16}H_{33} \\ | \quad\quad\quad\,\, \diagup \\ CH_2-C \end{array}$$ (108)

Analysis: calculated: N 7.95; found: N 7.2.

EXAMPLE 9

98.5 g (0.5 mole) of laurinlactam are reacted with 15 g (0.5 mole) of formaldehyde and 92.5 g of laurylamine as in Example 1. Toluene is used as solvent.
Yield: 197 g (=100%) of the compound of formula $$(CH_2)_{11} \begin{array}{c} C=O \\ \diagdown \\ N-CH_2-NH-C_{12}H_{25} \end{array}$$ (109)

Analysis: calculated: N 7.1; found: N 7.5.

EXAMPLE 10

(a) 211 g (1 mole) of N-methylol-β-methoxyphosphonopropionic acid amide are dissolved in 50 ml of water and the solution is treated with 85 g (0.1 mole) of methacrylic amide and 0.2 g of hydroquinone monomethyl ether.

The reaction solution is adjusted to a pH of 3 with 1 ml of concentrated hydrochloric acid and subsequently stirred for 6 hours at 50° C. Upon termination of the reaction, the reaction solution is adjusted to pH 7 with 2 ml of normal sodium hydroxide solution and filtered, to give 340 g of a 84% solution of the compound of formula $$(CH_3O)_2-\underset{\underset{O}{\|}}{P}-CH_2CH_2CONHCH_2NHCO-\underset{\underset{CH_3}{|}}{C}=CH_2$$ (110)

Yield: 100%.

Analysis: calculated: P 11.0; found: P 11.0.
Mass spectrum: M = 278 (theoretical value: 278).

(b) Example 10(a) is repeated with acrylic amide to give the compound of formula $$(CH_3O)_2\underset{\underset{O}{\|}}{P}-CH_2CH_2CONHCH_2NHCOCH=CH_2$$ (111)

in 98% yield.
Analysis: calculated: P 11.74; found: P 11.6.
Mass spectrum: M = 264 (theoretical value: 264).

EXAMPLE 11

133.5 g (0.5 mole) of N-methylol-β-diisopropoxyphosphonopropionic acid amide are reacted with 35.5 g (0.5 mole) of acrylic amide or 42.5 g (0.5 mole of methacrylic amide as in Example 10, to give the compounds of formulae $$[(CH_3)_2CHO]_2\underset{\underset{O}{\|}}{P}-CH_2CH_2CONHCH_2NHCO-CH=CH_2$$ (112)

and $$[(CH_3)_2CHO]_2\underset{\underset{O}{\|}}{P}-CH_2CH_2CONHCH_2NHCO-\underset{\underset{CH_3}{|}}{C}=CH_2$$ (113)

in 100% yield.

EXAMPLE 12

119.5 g (0.5 mole of N-methylol-β-diethyloxyphosphonopropionic acid amide are reacted with 35.5 g (0.5 mole) of acrylic amide as in Example 10, to give the compound of formula $$(C_2H_5O)_2\underset{\underset{O}{\|}}{P}-CH_2CH_2CONHCH_2NHCOCH=CH_2$$ (114)

in 100% yield.
Analysis: calculated: P 10.6; found: P 10.3.

EXAMPLE 13

85 g (1 mole) of methacrylic amide and 0.2 g of hydroxyquinone monomethyl ether are dissolved in 1000 ml of benzene. To this solution are added 30 g of paraformaldehyde. The solution is then warmed to 40° C. and a solution of 105 g (1 mole) of diethanolamine in 300 ml of benzene is added in the course of about 2 hours. The reaction mixture is then kept for a further 5 hours at 60° C. Upon termination of the reaction, the resultant compound precipitates as lower phase. It is isolated and freed from residual solvent, to give 178.5 g of a light yellow viscous compound of formula $$CH_2=\underset{\underset{CH_3}{|}}{C}-CONHCH_2N(CH_2CH_2OH)_2$$ (115)

Yield: 88.9%.
Analysis: calculated: N 13.85; found: N 13.4.

EXAMPLE 14

Copolymer of isobutylacrylate/methylmethacrylate/methacrylic amide-N-methylol monomethyl ether.

55.2 g (0.4 mole) of isobutylacrylate are dissolved in 150 ml of water and in the presence of 1 g of sodium lauryl sulphate. The polymerisation is initiated by addition of 0.1 g of potassium persulphate. Then 10 g (0.1 mole) of methylmethacrylate are added in the course of 35 minutes and the polymerisation is continued for 4½ hours at 75° C . Then 2 g (0.015 mole) of methacrylic amide-N-methylol monomethyl ether, dissolved in 100 ml of water, and 0.2 g of potassium persulphate are added, and the polymerisation is brought to completion after a further 3 hours at 85° C., to give 314 g of a viscous emulsion with a solids content of 21% (corresponding to a polymer yield of approx. 100%).

EXAMPLE 15

A polyamide carpet is padded with the following preparations at room temperature and squeezed out to a pick-up of 100%. The finished carpet is then dried for 30 seconds at 170° C.

Preparation (the amounts in g/l indicate the solids content):
A. 10 g/l of the compound obtained in Example 1 (in tetrachloroethylene)
B. 10 g/l of the compound obtained in Example 4 (in methanol/water 1:1).

The following results are obtained:

|  |  | A | B |
|---|---|---|---|
| fastness to rubbing | (dry) | 5 | 5 |
|  | (wet) | 5 | 5 |
| handle |  | soft | soft |
| antistatic effect |  | very good | very good |
| antisoil effect (dry): | treated | 4 | 4 |
|  | untreated | 3 | 3 |

The fastness to rubbing is evaluated by the rating 1 to 5 (5 = maximum rating).

The antisoil effect is evaluated with a Grey Scale (rating 1 to 5), in which the optimum is 5.

I claim:
1. A method of finishing synthetic organic fibrous material, in particular of providing it with an antistatic finish and optionally simultaneously improving the dirt repellency, which comprises applying at least one compound of formula

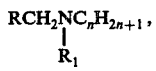

wherein R is

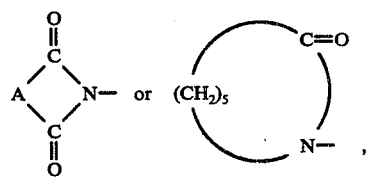

in which A is $-CH_2CH_2-$, $-CH=CH-$ or

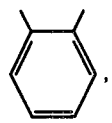

$R_1$ is hydrogen or $C_nH_{2n+1}$ and $n$ is an integer from 1 to 24, optionally in admixture with at least one homopolymer derived from the monomers of formulae

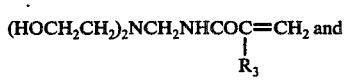

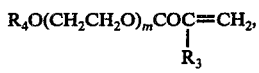

wherein $R_2$ is straight-chain or branched alkyl of 1 to 8 carbon atoms, $R_3$ is hydrogen or methyl, $R_4$ is alkyl of 1 to 6 carbon atoms and $m$ is an integer from 6 to 15, from aqueous or organic solutions or from emulsions to said material and subsequently drying it at elevated temperature.

2. A method according to claim 1 which comprises applying a compound of formula

wherein R' is

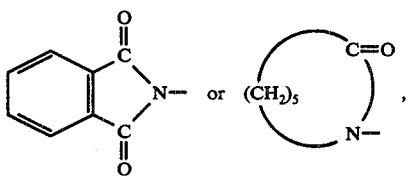

$R_1$ is hydrogen or $C_nH_{2n+1}$ and $n$ is an integer from 1 to 24.

3. A method according to claim 2, wherein each of $R_2$ and $R_4$ is alkyl of 1 to 4 carbon atoms, in particular methyl and ethyl, and $m$ is an integer from 6 to 10.

4. A method according to claim 2, wherein the mixture additionally contains further homopolymers or copolymers obtained from acrylic and methacrylic acid and the esters thereof with 1 to 18 carbon atoms in the ester moiety, or from acrylic amide and the N-methylol or N-methylol ether derivatives thereof.

5. Preparations for carrying out the process of claim 1 which contain 1 to 30 percent by weight of at least one compound of claim 1 and, optionally, 1 to 30 percent by weight of homopolymers.

6. Preparations according to claim 5 which are in the form of aqueous or organic solutions or emulsions.

7. Preparations for providing synthetic organic fibrous material with an antistatic finish and simultaneously improving the dirt repellency according to claim 5, which contain
(1) 1 to 30 percent by weight of a compound of formula

wherein R is

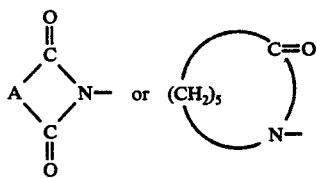 or 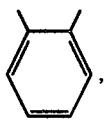

in which A is —CH$_2$CH$_2$—, —CH=CH— or

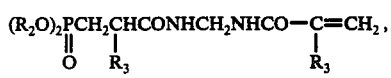

R$_1$ is hydrogen or C$_n$H$_{2n+1}$ and $n$ is an integer from 1 to 24, (2) 1 to 30 percent by weight of at least one homopolymer derived from monomers of formulae (R$_2$O)$_2$PCH$_2$CHCONHCH$_2$NHCO—C=CH$_2$,
∥  |                              |
O  R$_3$                          R$_3$ -continued

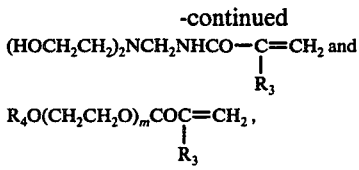

R$_4$O(CH$_2$CH$_2$O)$_m$COC=CH$_2$,
                    |
                    R$_3$ wherein R$_2$ is straight-chain or branched alkyl of 1 to 8 carbon atoms, R$_3$ is hydrogen or methyl, R$_4$ is alkyl of 1 to 6 carbon atoms and $m$ is an integer from 6 to 15, and, optionally (3) 1 to 30 percent by weight of further homopolymers or copolymers obtained from acrylic and methacrylic acid and esters thereof with 1 to 18 carbon atoms in the ester moiety, or from acrylic amide and the N-methylol or N-methylol ether derivatives thereof, the total amount of components (1) to (3) contained in said preparations being at most 60 percent by weight.

8. Preparations according to claim 7 which contain 1 to 20, preferably 1 to 10, percent by weight of components (1) to 20 percent by weight of component (2), and, optionally, 1 to 5 percent by weight of component (3).

9. The synthetic organic fibrous material finished according to the method of claim 1.

* * * * *

UNITED STATES PATENT AND TRADEMARK OFFICE
CERTIFICATE OF CORRECTION

PATENT NO. : 4,111,817
DATED : September 5, 1978
INVENTOR(S) : Horst Jäger

It is certified that error appears in the above–identified patent and that said Letters Patent are hereby corrected as shown below:

In claim 7, column 14, line 13, "1 to 30" should read

-- 1 to 10 --.

Signed and Sealed this

Eleventh Day of March 1980

[SEAL]

Attest:

Attesting Officer

SIDNEY A. DIAMOND

Commissioner of Patents and Trademarks